United States Patent
Suzuki et al.

(10) Patent No.: US 10,307,466 B2
(45) Date of Patent: Jun. 4, 2019

(54) COMPOSITION COMPRISING SOPHOROLIPID, PHYSIOLOGICALLY ACTIVE SUBSTANCE AND OIL OR FAT, AND METHOD FOR PRODUCING THE SAME

(71) Applicant: SARAYA CO., LTD., Osaka (JP)

(72) Inventors: Yasushi Suzuki, Osaka (JP); Hiromitsu Tabata, Osaka (JP); Mizuyuki Ryu, Osaka (JP); Nanase Ishii, Osaka (JP); Takashi Takeuchi, Tottori (JP); Yasuki Matsumura, Kyoto (JP); Kentaro Matsumiya, Kyoto (JP)

(73) Assignee: SARAYA CO., LTD., Osaka (JP)

( * ) Notice: Subject to any disclaimer, the term of this patent is extended or adjusted under 35 U.S.C. 154(b) by 193 days.

(21) Appl. No.: 15/124,432

(22) PCT Filed: Mar. 10, 2015

(86) PCT No.: PCT/JP2015/057059
§ 371 (c)(1),
(2) Date: Sep. 8, 2016

(87) PCT Pub. No.: WO2015/137357
PCT Pub. Date: Sep. 17, 2015

(65) Prior Publication Data
US 2017/0014489 A1   Jan. 19, 2017

(30) Foreign Application Priority Data

Mar. 10, 2014   (JP) .................................. 2014-046015

(51) Int. Cl.
| | | |
|---|---|---|
| A61K 31/7012 | (2006.01) |
| A61K 38/40 | (2006.01) |
| A61K 45/06 | (2006.01) |
| A23L 33/115 | (2016.01) |
| A23L 9/10 | (2016.01) |
| A23G 1/36 | (2006.01) |
| A61K 9/00 | (2006.01) |
| A61K 9/107 | (2006.01) |
| A61K 47/06 | (2006.01) |
| A61K 47/26 | (2006.01) |
| A61K 47/44 | (2017.01) |

(52) U.S. Cl.
CPC ................ *A61K 38/40* (2013.01); *A23G 1/36* (2013.01); *A23L 9/12* (2016.08); *A23L 33/115* (2016.08); *A61K 9/0053* (2013.01); *A61K 9/107* (2013.01); *A61K 45/06* (2013.01); *A61K 47/06* (2013.01); *A61K 47/26* (2013.01); *A61K 47/44* (2013.01); *A23V 2002/00* (2013.01)

(58) Field of Classification Search
CPC ................................................. A61K 31/7012
See application file for complete search history.

(56) References Cited

U.S. PATENT DOCUMENTS

| | | | |
|---|---|---|---|
| 5,756,471 A | 5/1998 | Hillion et al. | |
| 8,664,373 B2 | 3/2014 | Yanagisawa et al. | |
| 2006/0199244 A1* | 9/2006 | Ashby | .................... C12P 7/6463 |
| | | | 435/52 |
| 2008/0145411 A1 | 6/2008 | Shinagawa et al. | |
| 2008/0187593 A1 | 8/2008 | Bluth | |
| 2008/0193551 A1* | 8/2008 | De Waard | ............ A61K 9/2018 |
| | | | 424/535 |
| 2011/0223239 A1 | 9/2011 | Gross et al. | |
| 2011/0237531 A1* | 9/2011 | Yanagisawa | ............. A61K 8/60 |
| | | | 514/25 |
| 2012/0220464 A1* | 8/2012 | Giessler-Blank | ...... A01N 25/30 |
| | | | 504/329 |
| 2015/0112049 A1 | 4/2015 | Hirata et al. | |

FOREIGN PATENT DOCUMENTS

| | | |
|---|---|---|
| EP | 3042940 A1 | 7/2016 |
| JP | S61205449 A | 9/1986 |
| JP | H10501260 A | 2/1998 |
| JP | 2009062288 A | 3/2009 |
| JP | 2009531310 A | 9/2009 |
| JP | 2012036112 A | 2/2012 |
| JP | 2012232963 A | 11/2012 |
| WO | WO-2007130738 A1 | 11/2007 |
| WO | WO-2008044659 A1 | 4/2008 |
| WO | WO-2010050413 A1 | 5/2010 |
| WO | WO-2013129667 A1 | 9/2013 |
| WO | WO-2015034007 A1 | 3/2015 |
| WO | WO-2016013026 A1 | 1/2016 |

OTHER PUBLICATIONS

International Preliminary Report on Patentability in Application No. PCT/JP2015/057059 dated Sep. 22, 2016 (English Translation).
Supplementary European Search Report for Application No. EP 15760929, dated Oct. 19, 2017.
Ishll et al., "Transdermal administration of lactoferrin with sophorollpid," *Biochemistry and Cell Biology*, vol. 90, No. 3, pp. 504-512 (2012).
Sheetal Dhar et al., "Cytotoxicity of sophorolipid-gellan gum-gold nanoparticle conjugates and their doxorubicin loaded derivatives towards human glioma and human glioma stem cell lines," *Nanoscale Royal Society of Chemistry*, vol. 3, No. 2, pp. 575-580 (2011).
Inge N.A. Van Bogaert et al., "Microbial production and application of sophorolipids," *Applied Microbiology and Biotechnology*, vol. 76, No. 1, pp. 23-34 (2007).
Pradeep Kumar Singh et al., "From micron to nano-curcumin by sophorolipid co-processing: highly enhanced bioavailability, fluorescence, and anti-cancer efficacy," *Royal Society of Chemistry Advances*, vol. 4, No. 104, pp. 60334-60341 (2014).

(Continued)

*Primary Examiner* — Rosanne Kosson
(74) *Attorney, Agent, or Firm* — Marshall, Gerstein & Borun LLP

(57) ABSTRACT

The present invention provides an orally administered composition comprising a sophorolipid, a physiologically active substance, and an oil or fat, wherein the physiologically active substance exhibits an improved bioavailability.

17 Claims, No Drawings

(56) References Cited

OTHER PUBLICATIONS

Marcos Roberto de Oliveira et al., "Review: Sophorolipids A Promising Biosurfactant and it's Applications," *International Journal of Advanced Biotechnology and Research*, vol. 6, Issue 2, pp. 161-174 (2015).
International Search Report in International Application No. PCT/JP2015/057059, dated Jun. 16, 2015.
Gorin et al., "Hydroxy Fatty Acid Glycosides of Sophorose from Torulopsis Magnoliae", Can. J. Chem., vol. 39 (1961).

* cited by examiner

COMPOSITION COMPRISING SOPHOROLIPID, PHYSIOLOGICALLY ACTIVE SUBSTANCE AND OIL OR FAT, AND METHOD FOR PRODUCING THE SAME

TECHNICAL FIELD

The present invention relates to a physiologically active composition comprising a sophorolipid and exhibiting an improved bioavailability of a physiologically active substance and to a method for producing the composition.

BACKGROUND ART

Sophorolipids are known as a class of biosurfactants of biological origin. Sophorolipids are obtained by fermentation of a yeast (Non-Patent Literature 1). Sophorolipids are easily produced by a simple process involving, for example, inoculation of a yeast in liquid medium supplemented with a carbon source such as a sugar (e.g., glucose) and a vegetable oil or fat, and culture with aeration and agitation at moderate temperature under moderate pressure. Sophorolipids can be produced in large quantities, are highly safe and has other advantages. Due to these features, sophorolipids are used in combination with a physiologically active substance and are applied to various fields including the detergent, pharmaceutical, cosmetics, and food sectors (Patent Literature 1).

A physiologically active substance, however, even when orally administered in combination with a sophorolipid, is often degraded by digestive juices such as the saliva, gastric juice and intestinal juice, or its bioavailability through intestinal absorption is not always meet the requirements.

CITATION LIST

Patent Literature

Patent Literature 1: JP 2009-62288 A

Non-Patent Literature

Non-Patent Literature 1: Gorin, Can. J. Chem., 39, 846 (1961).

SUMMARY OF INVENTION

Technical Problem

The inventors have performed various investigations and experiments over a long period of time with repeated trial and error to solve the above problems. The inventors, as a result, have unexpectedly found that a composition comprising a sophorolipid, a physiologically active substance, and an oil or fat surprisingly solves all the above problems. The inventors have further conducted studies and completed the present invention.

Solution to Problem

That is, the present invention relates to the following aspects.
[1] A composition comprising a sophorolipid, a physiologically active substance, and an oil or fat.
[2] The composition of the above [1], wherein the physiologically active substance exhibits an improved bioavailability.
[3] The composition of the above [1] or [2], which is orally administered.
[4] The composition of any one of the above [1] to [3], wherein the physiologically active substance exhibits resistance to degradation by digestive juices.
[5] The composition of any one of the above [1] to [4], wherein the oil or fat is at least one or more oils or fats selected from the group consisting of squalene, soybean oil, rapeseed oil, cottonseed oil, sesame oil, safflower oil, sunflower oil, corn oil, rice bran oil, peanut oil, cacao butter, and medium-chain fatty acid glycerides having 8 to 10 carbon atoms.
[6] The composition of any one of the above [1] to [5], wherein the sophorolipid is an acidic sophorolipid and/or a lactonic sophorolipid.
[7] The composition of any one of the above [1] to [6], wherein the physiologically active substance is a physiologically active substance that is intestinally absorbable.
[8] The composition of the above [7], wherein the physiologically active substance that is intestinally absorbable is lactoferrin.
[9] The composition of the above [8], wherein the lactoferrin enhances the analgesic effect of morphine.
[10] The composition of any one of the above [1] to [7], wherein the physiologically active substance is a fat-soluble physiologically active substance selected from
vitamins selected from vitamin A, vitamin D, vitamin E, vitamin K, and derivatives thereof,
polyunsaturated fatty acids selected from docosahexaenoic acid, eicosapentaenoic acid, α-linolenic acid, γ-linolenic acid, linoleic acid, and arachidonic acid,
ubiquinones, menaquinones, and phylloquinones having an isoprenoid side chain, such as coenzyme $Q_{10}$,
carotenoids selected from α-carotene, β-carotene, γ-carotene, lycopene, β-cryptoxanthin, lutein, zeaxanthin, canthaxanthin, and astaxanthin,
steroids selected from ergosterol and stigmasterol,
fat-soluble polyphenols selected from curcumin, quercetin, and cinnamic acid,
flavonoids selected from isoflavone, anthocyanidin, and hesperidin,
tannins selected from catechin and proanthocyanidin,
saponins obtained from plants selected from *Panax notoginseng, Panax ginseng*, soybeans, cucumbers, yucca, jiaogulan (*Gynostemma pentaphyllum*), and *Sapindus mukorossi*,
lignans selected from sesamin and sesaminol,
triterpenes selected from cucurbitacin and limonene, and
α-lipoic acid, or
a water-soluble physiologically active substance selected from
vitamins selected from vitamin $B_1$, vitamin $B_2$, niacin, pantothenic acid, vitamin $B_6$, biotin, folic acid, vitamin $B_{12}$, vitamin C, and derivatives thereof,
amino acids selected from glycine, alanine, valine, leucine, isoleucine, phenylalanine, tyrosine, tryptophan, serine, threonine, proline, hydroxyproline, cysteine, methionine, aspartic acid, glutamic acid, lysine, arginine, histidine, and carnitine,
polyphenols, flavonoids and flavonoid glycosides selected from chlorogenic acid, tannin, catechin, flavonoid, lignan, lignin, coumarin, and theaflavin, peptides selected from a soybean peptide, a sardine peptide, a marine peptide, a casein phosphopeptide, a whey peptide, a wheat peptide, and a corn peptide, triterpene glycosides selected from those derived from *Siraitia grosvenorii* and licorice, and minerals selected from calcium, magnesium, iron, zinc, potassium, sodium, copper, vanadium, manganese, selenium, molybdenum, cobalt, and compounds to which these minerals are bound.

[11] The composition of any one of the above [1] to [10], which is a medicament.

[12] The composition of any one of the above [1] to [10], which is a food product.

[13] The composition of any one of the above [1] to [10], which is a supplement.

[14] A method for producing the composition of the above [1], the method comprising mixing a sophorolipid, a physiologically active substance, and an oil or fat.

The physiologically active substance may be any compound with a physiological activity. The physiologically active substance may be a fat- and water-soluble physiologically active substance. The physiologically active substance is not limited to the above exemplified compounds and may be a compound similar to them. The physiologically active substance may be, for example, folic acid, GABA, caffeine, sesamin, theophylline, theobromine, leucine, isoleucine, valine, glycine, anserine, glutathione, curcumin, glycyrrhizin, taurine, or the like.

Advantageous Effects of Invention

The composition provided by the present invention is useful as an ideal medicament or food product with the following excellent effects.
1. The composition exhibits an excellent bioavailability of a physiologically active substance.
2. The physiologically active substance is efficiently incorporated into the body especially when the composition is orally administered.
3. The physiologically active substance exhibits resistance to degradation by digestive juices.
4. The physiologically active substance is efficiently absorbed through the intestinal tract.
5. The sophorolipid exhibits resistance to degradation.

DETAILED DESCRIPTION OF THE INVENTION

Sophorolipids are glycolipids that consist of a hydroxyl fatty acid and sophorose or a sophorose derivative in which the hydroxyl groups are partially acetylated. Sophorose is a sugar formed from two glucose molecules linked via a β1,2 bond. A hydroxyl fatty acid is a fatty acid with a hydroxyl group. Sophorolipids are generally found in two forms: acidic and lactonic. In acidic sophorolipids, the carboxyl end of the hydroxy fatty acid is free. In lactonic sophorolipids, the carboxyl end of the hydroxy fatty acid is internally linked with sophorose. Acidic sophorolipids are represented by, for example, general formula (1). Lactonic sophorolipids are represented by, for example, general formula (2). Sophorolipids contained in culture medium resulting from fermentation of a yeast are a mixture of sophorolipids of general formulae (1) and (2). Such a mixture can be obtained as a collection of 30 or more structural analogs, including sophorolipids with different fatty acid chain lengths ($R^3$) and sophorolipids with acetylation or protonation at the 6' ($R^2$) or 6" ($R^1$) position of sophorose.

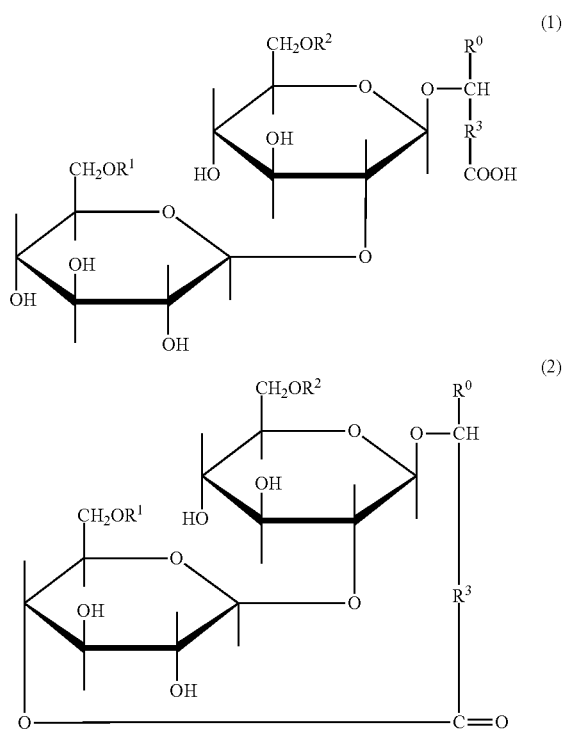

In general formulae (1) and (2), $R^0$ is hydrogen or a methyl group. $R^1$ and $R^2$ are each independently hydrogen or an acetyl group. $R^3$ is a saturated aliphatic hydrocarbon chain or an unsaturated aliphatic hydrocarbon chain having at least one double bond, and may have one or more substituents. The substituents may be any substituent that does not impair the advantageous effects of the invention. Examples of the substituents include a halogen, a hydroxyl group, a lower ($C_{1-6}$) alkyl group, a halo lower ($C_{1-6}$) alkyl group, a hydroxy lower ($C_{1-6}$) alkyl group, and a halo lower ($C_{1-6}$) alkoxy group. The carbon number of $R^3$ is typically 11 to 20, preferably 13 to 17, and more preferably 14 to 16.

The sophorolipid used in the present invention may be acidic forms (general formula (1)), in which the carboxyl end of the hydroxy fatty acid is free, or lactonic forms (general formula (2)), in which the carboxyl end of the hydroxy fatty acid is internally linked with sophorose.

The sophorolipid used in the present invention is produced by a known method and is preferably produced by, for example, culture of a yeast.

A sophorolipid-containing liquid obtained by yeast fermentation is not particularly limited as long as the advantageous effects of the invention are not impaired, but may be a liquid containing natural sophorolipids or a liquid prepared by separating lactonic sophorolipids from natural sophorolipids. In terms of the cost etc., preferred is a liquid containing natural sophorolipids. Here, the term "natural sophorolipids" means a sophorolipid fraction separated from culture medium obtained by culturing a yeast, and typically refers to a mixture of acidic sophorolipids and lactonic sophorolipids.

Examples of the yeast include *Starmerella* (*Candida*) *bombicola*, *C. apicola*, *C. petrophilum*, *Rhodotorula* (*Candida*) *bogoriensis*, *C. batistae*, *C. gropengiesseri*, *Wickerhamiella domercqiae*, and *Yarrowia lipolytica*. Culture of such a yeast in a conventional manner can produce sophorolipids. The yeast strain may be a strain purchased from a microorganisms depositary, and the purchased strain may be passaged before use. *Rhodotorula* (*Candida*) *bogoriensis* NRCC 9862 produces 13-[(2'-O-β-D-glucopyranosyl-β-D-glucopyranosyl)oxy]docosanoic acid 6',6"-diacetate, which is a sophorolipid having a glycoside bond between sophorose and the hydroxyl group at the center of the alkyl chain. This sophorolipid is different from general formula (1) or (2), but the sophorolipid and general formulae (1) and (2) are in common in that they all contain sophorose and a hydroxyl fatty acid. Such a sophorolipid is also included in the sophorolipid used in the present invention.

Preferably, culture of a yeast to produce sophorolipids is performed by, for example, simultaneously adding a sugar and a hydrophobic oily substrate to culture medium at high concentrations. The culture method is not limited to this method, and any known methods can be widely used as long as the advantageous effects of the invention are not impaired. The known culture method used may be those disclosed in, for example, JP 2002-045195 A. Specifically, culture may be performed by a method in which *Starmerella* (*Candida*) *bombicola* is cultured as a sophorolipid-producing yeast in culture medium supplemented with a carbon source containing glucose as a sugar and containing a fatty acid and a vegetable oil as hydrophobic oily substrates.

The composition of the culture medium is not limited to a particular one. However, the fatty acid tail of sophorolipids is known to vary depending on the fatty acid chain length and the amount of the hydrophobic substrate added to the culture medium. Hence the properties of the fatty acid tail of sophorolipids can be controlled to some extent. The hydrophobic substrate suitable for the culture is, for example, oleic acid or a lipid containing a high proportion of oleic acid. Examples of such a lipid include vegetable oils such as palm oil, rice bran oil, rapeseed oil, olive oil and safflower oil, and animal fats and oils such as lard and beef tallow. Addition of a mixed hydrophobic substrate of triglyceride and oleic acid to culture medium will result in the production of a high proportion of sophorolipids containing oleic acid in large quantities with a high yield. In the industrial application, the fermentation is required to produce sophorolipids in large quantities with a high yield. In this case, the carbon source is preferably a mixture of a hydrophilic sugar and a hydrophobic oil or fat. The hydrophilic substrate usually used is glucose. The culture conditions of a yeast for producing sophorolipids have been well established, and the culture in the present invention may be performed in accordance with these conditions.

After culture, the resulting culture medium is collected by, for example, centrifugation, decantation or other techniques, and then washed with water to give a liquid containing natural sophorolipids. The technique for collecting a liquid containing natural sophorolipids from the culture medium may be any technique that does not impair the advantageous effects of the invention. The collection may be performed by a known technique, such as those disclosed in JP 2003-9896 A, for example. In a specific purification process, the pH of the final culture medium containing sophorolipid precipitates is adjusted so that the solubility of the sophorolipid precipitates in water is appropriately controlled, and in the subsequent step, the natural sophorolipids are collected as a crude product with a water content of about 50 wt % without using any organic solvent.

The sophorolipid used in the present invention may be acidic and/or lactonic sophorolipids as described above. The proportion of acidic sophorolipids contained is preferably 20 wt % or more, more preferably 50 wt % or more, even more preferably 70 wt % or more, particularly preferably 80 wt % or more, and most preferably 90 wt % or more.

The proportion of acidic sophorolipids in the crude product of natural sophorolipids can be increased by a known technique, and any known techniques can be widely used as long as the advantageous effects of the invention are not impaired. The proportion of acidic sophorolipids may be increased by, for example, mixing the crude product of natural sophorolipids obtained in the above procedure with an aqueous sodium hydroxide solution, then heating the mixture to allow hydrolysis to occur, and adjusting the pH with addition of a pH adjuster.

Examples of the pH adjuster include inorganic acids such as sodium hydrogen carbonate, sulfuric acid, hydrochloric acid, nitric acid, phosphoric acid, boric acid, and hydrofluoric acid; and organic acids such as formic acid, acetic acid, malic acid, citric acid, oxalic acid, glutamic acid, and aspartic acid.

The sophorolipid in the present invention may be a highly purified acidic sophorolipids.

The highly purified acidic sophorolipids can be produced by a method comprising
(i) the step of adjusting the pH of a liquid containing acidic sophorolipids to an acidic region (hereinafter also called step (i)), and
(ii) the step of subjecting the acidic liquid containing acidic sophorolipids resulting from the step (i) to chromatographic separation (hereinafter also called step (ii)).

These steps will be described in detail below.

The step (i) is adjusting the pH of a liquid containing acidic sophorolipids to an acidic region. In the acidic region, the carboxyl groups are protonated to allow formation of stable, dense supramolecular structure of acidic sophorolipids.

The acidic region is preferably at a pH range of less than about 7, which is the pKa value of acidic sophorolipids, more preferably a pH range of about 1 to 6, and even more preferably a pH range of about 3 to 5. These acidic regions are advantageous in that acidic sophorolipids form stable supramolecular structure, that impurities such as fermentation by-products are efficiently removed in the subsequent steps, and that highly purified acidic sophorolipids are collected at a higher recovery rate. In addition, by adjusting the pH to these ranges, the molecules of acidic sophorolipids are oriented in one direction and the supramolecular structure is easily formed. As a result, much highly purified, more stable acidic sophorolipids are obtained.

The adjustment of the acidic liquid containing acidic sophorolipids to the acidic region may be achieved by any technique as long as the advantageous effects of the invention are not impaired, and any known techniques can be widely used. The pH adjuster that can be used in this adjustment include, for example, inorganic acids such as sodium hydrogen carbonate, sulfuric acid, hydrochloric acid, nitric acid, phosphoric acid, boric acid, and hydrofluoric acid; and organic acids such as formic acid, acetic acid, malic acid, citric acid, oxalic acid, glutamic acid, and aspartic acid.

The step (ii) is subjecting the acidic liquid containing acidic sophorolipids resulting from the step (i) to chromatographic separation.

The sophorolipid-containing liquid to be subjected to chromatographic separation preferably has a viscosity of about 5 to 50 mPa·s and more preferably about 5 to 20 mPa·s to achieve adequate separation efficiency. When the sophorolipid-containing liquid has a higher viscosity, the viscosity is preferably adjusted to these ranges. The adjustment of the viscosity may be achieved by any technique as long as the advantageous effects of the invention are not impaired, but preferably the liquid is diluted with ethanol or purified water, which has no harmful effects on a human body or the environment.

The column filler (adsorbent) used as the stationary phase in the chromatography may be any filler known in the art, such as silica gel, an octadecyl silica gel (ODS) resin, an ion exchange resin, and a synthetic adsorbent. The chromatography is preferably reversed-phase chromatography, which allows the use of a highly safe solvent as the eluent (development phase). When reversed-phase chromatography is used, the filler is more preferably an ODS resin etc. Use of an ODS resin composed of hydrophobic octadecyl groups etc. chemically bonded to a silica gel support allows a hydrophobic interaction to occur with the alkyl side chain of the sophorolipids, thereby enabling more efficient production of a liquid containing highly purified sophorolipids. The eluent for reversed-phase chromatography is preferably a solvent with a higher polarity than that of the filler in view of separation efficiency etc. Preferred examples of such an eluent include methanol and ethanol, and particularly preferred is ethanol in view of safety.

In this manner, an elution fraction containing sophorolipids is obtained and is then typically processed into a powder.

The sophorolipid-containing liquid is processed into a powder by any technique as long as the advantageous effects of the invention are not impaired. The liquid is processed into a powder by a known technique, such as freeze-drying, recrystallization, spray-drying, etc. Preferred is spray-drying in view of the production efficiency. The spray-drying may be performed with or without using an excipient. The spray-drying conditions are not particularly limited as long as the advantageous effects of the invention are not impaired, but spray-drying at a high temperature and a high rotational speed (e.g., at a temperature of about 100° C. or more and at a rotational speed of about 12,000 rpm or more) allows the production of a sophorolipid powder with a high flowability and with a few aggregations.

The sophorolipid powder of the present invention may contain a component other than sophorolipids if desired. Examples of the component include carbohydrates such as dextrin, protein-containing materials such as skim milk, powdery oil and fat materials, vitamins, minerals, plant sterols, lactic acid bacteria powders, and other powdery materials usable in foods. The sophorolipid powder of the present invention is preferably granulated by a known granulation process such as fluidized bed granulation process. The granulation is particularly preferably performed by using a tumbling fluidized bed coating machine to provide better flowability to the powder. The average particle size of the powder after granulation is preferably about 300 μm or less and more preferably about 200 μm or less. The term "average particle size" herein is defined as a particle size when the cumulative weight reaches 50% in the particle size distribution determined by sieving.

The amount of sophorolipids contained in the composition cannot be specifically defined, but is, for example, typically 0.0001 to 99.9999 wt %, preferably 0.01 to 20 wt %, and more preferably 0.1 to 10 wt % based on the total weight of the composition.

The oil or fat used in the present invention may be a solid oil or fat or a liquid oil.

The term "solid oil or fat" herein refers to an oil or fat that is in a solid form at normal temperature (25° C.), with the exception of a certain type. Examples of the solid oil or fat usable in the present invention include squalene, trilaurin (glycerol trilaurate), trimyristin (glycerol trimyristate), tripalmitin (glycerol tripalmitate), tristearin (glycerol tristearate), hardened beef tallow, hardened lard, hydrogenated fish oil, hardened rapeseed oil, hardened soybean oil, and hardened palm oil.

The term "liquid oil" herein refers to an oil that is in a liquid form at normal temperature (25° C.), with the exception of a certain type. Specific examples of the liquid oil usable in the present invention include soybean oil, corn oil, cottonseed oil, sunflower oil, walnut oil, olive oil, castor oil, almond oil, safflower oil, apricot kernel oil, avocado oil, evening primrose oil, wheat germ oil, kukui nut oil, grapeseed oil, cocoa butter, coconut oil, rapeseed oil, peanut oil, rice bran oil, sesame oil, palm kernel oil, palm oil, jojoba oil, macadamia nut oil, shea butter, mango butter, kokum butter, whale oil, sardine oil, and squid oil. The liquid oils may be purified oils, such as a light tasting vegetable oil, or unpurified oils.

The amount of the oil or fat contained in the composition cannot be specifically defined, but is, for example, typically about 0.0001 to 99.9999 wt %, preferably about 0.01 to 20 wt %, and more preferably about 0.1 to 10 wt % based on the total weight of the composition.

The physiologically active substance used in the present invention is not limited to a particular substance, but is preferably a physiologically active substance that is intestinally absorbable. Such a physiologically active substance may be exemplified by vitamin A, the vitamin B family, vitamin C, vitamin D, vitamin E, vitamin K, peptides, polyunsaturated fatty acids such as DHA and EPA, and glycosides from *Siraitia grosvenorii*. The physiologically active substance may be any substance that provides a desired physiological activity to the body. The physiologically active substance may be lactoferrin, which has the physiological action that enhances the analgesic effect of an analgesic drug, such as morphine. In cases where lactoferrin is used, lactoferrin and an analgesic substance may be administered by the same route or different routes.

The amount of the physiologically active substance used cannot be specifically defined, but is, for example, typically about 0.001 to 99.999 wt %, preferably about 0.01 to 20 wt %, and more preferably about 0.1 to 10 wt % based on the total weight of the composition.

The composition of the present invention may further comprise a cyclodextrin. The cyclodextrin may be any cyclodextrin that does not impair the advantageous effects of the invention, and may be, for example, one or more selected from α-cyclodextrin, β-cyclodextrin, γ-cyclodextrin, and derivatives thereof. Examples of the derivatives include branched cyclodextrins and cyclodextrins having substituents including a methyl group, a hydroxypropyl group, and an acetyl group. Of the cyclodextrins, preferred are α-cyclodextrin, β-cyclodextrin, γ-cyclodextrin, etc. in view of achieving adequate storage stability.

The amount of the cyclodextrin contained in the sophorolipid composition of the present invention is not limited to a particular value, but is preferably about 50 wt % to 99 wt % and more preferably about 80 wt % to 95 wt %. When the cyclodextrin is contained in these amounts, bitterness and the smell of the yeast are masked and the physiological activity of the sophorolipid is effectively exerted. The amount of the sophorolipid contained in the sophorolipid powder of the present invention is preferably about 1 to 120 parts by mass, more preferably about 1 to 80 parts by mass, and even more preferably about 20 to 80 parts by mass based on 100 parts by mass of the cyclodextrin in view of achieving adequate storage stability, for example, preventing deliquescence.

An emulsifier may be used in the present invention. The term "emulsifier" herein refers to a substance that adsorbs to or aligns itself on the boundary surface (interface) between two substances with different properties, such as water and oil, and then greatly alter the properties of the interface. Various types of such substances that are acceptable in foods can be used as the emulsifier in the present invention.

Examples of the emulsifier herein include lecithins, monoacylglycerols, and/or diacylglycerols. Particularly preferred is a lecithin, which has a relatively low HLB value and can be produced from natural products such as soybeans.

When a monoacylglycerol or a diacylglycerol is used as the emulsifier, the fatty acids contained in the monoacylglycerol or the diacylglycerol are preferably, for example, stearic acid, palmitic acid, myristic acid, and lauric acid, and are particularly preferably palmitic acid.

The production method of the present invention comprising mixing an oil or fat, a sophorolipid, and a physiologically active substance. A mixture of these ingredients are preferably prepared by preparing an oil phase and an aqueous phase, then mixing the two phases, and heating the mixture to effect emulsification. The oil phase herein can contain a fat-soluble physiologically active substance, an emulsifier, etc. in addition to the oil or fat. The aqueous phase can contain a water-soluble physiological active substance, a pH adjuster, water, etc. in addition to the sophorolipid.

Preferably, the oil phase and the aqueous phase are separately heated, then the aqueous phase is added to the oil phase while the oil phase is stirred at high speed, thereby effecting emulsification.

The physiologically active substance can be added to the oil phase and/or the aqueous phase or can be added to the mixture obtained after emulsification of the oil phase and the aqueous phase.

The temperature during the emulsification process is preferably 0 to 100° C., more preferably 20 to 80° C., and most preferably 40 to 60° C. in view of achieving good bioavailability of the physiologically active substance.

The stirring for mixing and emulsifying the oil phase and the aqueous phase is preferably performed at 500 rpm to 20,000 rpm, more preferably 5,000 to 15,000 rpm, and most preferably 8,000 to 12,000 rpm, but the stirring conditions are not limited thereto.

The composition of the present invention, when used as a medicament, is preferably used as follows.

The composition can be administered systemically or locally and can be administered orally or parenterally. The dosage may vary with the age, body weight, and symptoms of the subject, the type of the physiologically active substance, etc., but the composition can be typically administered to an adult human at a dose ranging from 0.1 mg to 1 g, once to several times a day. The compound of the present invention can be administered to humans as well as non-human animals, in particular, non-human mammals.

The compound of the present invention can contain appropriate additives such as a diluent, a dispersant, an adsorbent, and a solubilizer to provide a pharmaceutical formulation, including solid or liquid compositions for oral administration and injections for parenteral administration. The pharmaceutical composition of the present invention may be in a known dosage form, such as injections, eye drops, liquids, capsules, troches, aerosols, elixirs, suspensions, emulsions, and syrups.

The pharmaceutical composition of the present invention in the form of a solid formulation, such as tablets, pills, powders and granules, may contain an additive, such as lactose, mannitol, glucose, hydroxypropyl cellulose, microcrystalline cellulose, starch, polyvinyl hydrin, magnesium aluminometasilicate, and silicic anhydride powder. If needed, the pharmaceutical composition in the form of tablets or pills may be coated with a film of a substance that is soluble in the stomach or intestinal tract, such as sucrose, gelatin, hydroxypropyl cellulose, and hydroxymethyl cellulose phthalate, or the pharmaceutical composition may be a multilayer tablet containing two or more layers.

The pharmaceutical composition of the present invention also includes capsules prepared by dissolving the compound of the present invention in a solvent, then adding an additive to the solution, and filling empty capsules with the resulting liquid, semisolid, or solid mixture. The solvent may be water, purified water, ethanol, or a vegetable oil. Of them, preferred are ethanol, water, and a mixture of purified water and ethanol. The additive may be any additive commonly used for the production of capsules, and such an additive can be used without any particular limitation. Examples of the additive include glycerol; propylene glycol fatty acid esters; low molecular weight polyethylene glycols such as polyethylene glycol 200 to 600, glycerol fatty acid esters thereof, medium-chain fatty acid triglycerides; alcohols/polyhydric alcohols such as stearyl alcohol, cetanol, polyethylene glycol, and esters thereof; oils and fats such as sesame oil, soybean oil, peanut oil, corn oil, hardened oils, paraffin oil, and white beeswax; triethyl citrate; and fatty acids such as triacetin, stearic acid, palmitic acid, and myristic acid and derivatives thereof. These additives are suitable for the preparation of a liquid or semisolid capsule content. A preferred additive for the capsules of the present invention is a propylene glycol fatty acid ester. Examples of the propylene glycol fatty acid ester include propylene glycol monocaprylate (Capmul PG-8 (trade name), Sefol 218 (trade name), Capryol 90 (trade name)), propylene glycol monolaurate (Lauroglycol FCC (trade name)), propylene glycol monooleate (Myverol P-O6 (trade name)), propylene glycol myristate, propylene glycol monostearate, propylene glycol ricinoleate (Propymuls (trade name)), propylene glycol dicaprylate/dicaprate (Captex (registered trademark) 200 (trade name)), propylene glycol dilaurate, propylene glycol distearate, and propylene glycol dioctanoate (Captex (registered trademark) 800 (trade name)). The capsule shells used in the present invention may be made of any material, and examples of the capsule material include naturally occurring polysaccharides, such as agar-agar, alginates, starch, xanthan, and dextran; proteins such as gelatin and casein; and chemically processed materials, such as hydroxy starch, pullulan, hydroxypropyl cellulose, hydroxypropyl methyl cellulose, polyvinyl alcohol and its derivatives, polyacryl derivatives, polyvinylpyrrolidone and its derivatives, and polyethylene glycol.

The pharmaceutical composition of the present invention in the form of a pharmaceutically acceptable liquid formulation for oral administration, such as emulsions, solutions, suspensions, syrups, and elixirs, may contain a diluent, such as water, purified water, ethanol, a vegetable oil, and an emulsifier. In addition to such a diluent, the liquid formulation may contain a pharmaceutical aid, such as a wetting agent, a suspending agent, a sweetener, a flavor, an aroma, and an antiseptic.

The food product of the present invention may be a processed food, a cooked food, etc. The composition of the present invention may be used as an ingredient or a food additive for such foods.

Specific examples of the cooked food using the ingredient or the food additive include fried dishes; shoestring fries (including French fries); seasoned and deep-fried meat and fish dishes; tempuras; croquettes; cutlets; skewered dishes; grilled fish dishes with soy sauce-based sauce; teriyaki dishes; Japanese or western simmered dishes; soups and potages; Chinese dishes such as sweet-and-sour pork, Japanese chop-suey, and shrimps with chili sauce; gratins; curries and stews; sauces such as meat sauce and thick starchy sauce; egg dishes such as Japanese rolled omelet, Japanese thick rolled omelet, thin omelet cut into narrow strips, omelet, and Japanese steamed egg custard; rice dishes such as steamed rice, sticky rice steamed with adzuki beans, rice balls, sticky rice dumplings wrapped in bamboo (zongzi), Japanese rice dishes cooked in an iron pot, sushi, fired rice, pilafs, fried rice with chicken, dry curry rice, rice gratins, Japanese rice soup (zosui), rice porridge, rice cakes, and sweet rice balls covered with adzuki bean paste; meat dishes such as Hamburg steaks, meatballs, Chinese dumplings, shumai, spring rolls, grilled meat dishes, grilled meat dishes with teriyaki sauce, sukiyaki, Japanese grilled mutton dishes, Japanese style of skewered chicken, meat loaf, fried chicken, and chicken nuggets; fish paste products and dishes using fish paste products, such as Japanese stew (oden); toppings for Japanese rice bowl dishes such as rice bowl dishes topped with a deep-fried pork cutlet, rice bowl dishes topped with simmered chicken and egg, rice bowl dishes topped with stir-fried vegetables, and rice bowl dishes topped with tempura; noodles such as wheat noodles, buckwheat noodles, fired wheat noodles with sauce flavor, Chinese-style wheat noodles, and wontons; pastas such as macaronies and spaghetti; processed wheat foods such as pies, pizzas, Japanese savory pancakes (okonomiyaki), ball-shaped Japanese snacks made of a wheat-flour-based batter (takoyaki), adzuki bean paste-filled steamed buns, meat-filled steamed buns, bread, cakes, doughnuts, and pancakes; processed bean foods such as tofu, fried tofu fritters, fermented soybeans, and sweet simmered red kidney beans; sweets such as candies, thick jellied desserts made of adzuki bean paste, agar and sugar (yokan), jellies, puddings, Bavarian cream, chocolate, yogurt, fresh cream, whipped cream, Japanese fish-shaped cakes (taiyaki), and cookie dough; fruit juice (fruit drinks); and konjac. Of these, the composition of the present invention is preferably used in chocolate, ice creams, jellies, etc.

EXAMPLES

The composition of the present invention will be specifically described below, but the Examples are provided only for the illustrative purposes. The present invention is not limit to these Examples.

In the Examples below, the sign "%" refers to "wt %" unless otherwise specified.

(1) Preparation of Compositions

Example 1

Squalene (Maruha Nichiro Foods, Inc.), soybean lecithin (SLP-paste, Tsuji Oil Mills Co., Ltd.) and glycerol (Kao Corporation) were mixed to prepare an oil phase. Separately, a sophorolipid, bovine lactoferrin (bLF) (MLF-1, Morinaga Milk Industry Co., Ltd.), sodium hydrogen carbonate (sodium bicarbonate, Asahi Glass Co., Ltd.) and water were mixed to prepare an aqueous phase (see Table 1). The phases were then heated to 80° C. The aqueous phase was added to the oil phase that was stirred at a high speed (10,000 rpm) with a high-speed stirrer (homogenizer HG-200, As One Corporation) to give the composition of Example 1. The sophorolipid used was prepared and purified in accordance with a known method (JP 2003-9896 A).

Example 2

Squalene, soybean lecithin and glycerol were mixed to prepare an oil phase. Separately, the sophorolipid, sodium hydrogen carbonate and water were mixed to prepare an aqueous phase (see Table 1). The phases were then heated to 80° C. The aqueous phase was added to the oil phase that was stirred at a high speed. The mixture of the oil phase and the aqueous phase was stirred for 10 minutes to effect emulsification. After the mixture was allowed to cool back to 40° C. or less, bovine lactoferrin (bLF) and water were added to give the composition of Example 2.

Example 3

The composition of Example 3 was prepared in the same manner as in Example 2 except that the components of the oil phase and the aqueous phase were as described in Example 3 in Table 1.

Comparative Example 1

The composition of Comparative Example 1 was prepared in the same manner as in Example 1 except that the components of the oil phase and the aqueous phase were as described in Comparative Example 1 in Table 1.

The components of the compositions of Examples 1 to 3 and Comparative Example 1 are shown in Table 1.

TABLE 1

| | | Example 1 | Example 2 | Example 3 | Comparative Example 1 |
|---|---|---|---|---|---|
| Oil phase | Squalene | 2.00% | 2.00% | 2.00% | 2.00% |
| | Soybean lecithin (50%) | 0.50% | 0.50% | 5.00% | 0.50% |
| | Sucrose fatty acid ester | — | — | — | 2.50% |
| | Glycerol | 5.00% | 5.00% | 5.00% | 5.00% |
| Aqueous phase | Sophorolipid | 2.50% | 2.50% | 0.50% | — |
| | Bovine lactoferrin | 5.00% | — | — | 5.00% |
| | Sodium hydrogen carbonate | 0.20% | 0.20% | 0.10% | 0.10% |
| | Water | q.s. for 100% | q.s. for 100% | q.s. for 100% | q.s. for 100% |
| After emulsification | Bovine lactoferrin | — | 5.00% | 5.00% | — |
| | Water | — | 20.00% | 20.00% | — |
| | Total | 100% | 100% | 100% | 100% |

(2) Experiment 1: Evaluation of Analgesic Effect

For the evaluation of an analgesic effect, the tail-flick test was performed with 48° C. heat stimulation. In the tail-flick test, the tail of mice is exposed to heat stimulation, and latency for the animal to flick the tail is measured. The response latency is known to be delayed after administration of an analgesic drug such as morphine. The test is used for the evaluation of an analgesic effect.

ICR mice at 5 weeks old were subjected to daily simultaneous administration of an intraperitoneal dose of morphine (3 mg/kg) (morphine hydrochloride (trade name), Daiichi Sankyo) and an oral dose of one of the compositions of Examples 1 to 3 (300 mg/kg bLF) and Comparative Example 1 (300 mg/kg) for 5 days. At 30 and 90 minutes after the administration on day 5, the tail-flick test was performed.

As a treatment control, ICR mice at 5 weeks old were subjected to daily simultaneous administration of an intraperitoneal dose of morphine (3 mg/kg) and an oral dose of physiological saline for 5 days. The tail-flick test was then performed in the same manner as above.

As a negative control, daily simultaneous administration of an intraperitoneal dose of physiological saline and an oral dose of physiological saline was performed for 5 days. As a positive control, ICR mice at 5 weeks old were subjected to daily simultaneous administration of an intraperitoneal dose of morphine (3 mg/kg) and an oral dose of bLF for 5 days. The tail-flick test was then performed in the same manner as above.

The experimental results using the compositions of Examples 1 to 3 and Comparative Example 1 are shown in Table 2.

TABLE 2

|  | Evaluation at 30 min | Evaluation at 90 min |
|---|---|---|
| Example 1 | +++ | +++ |
| Example 2 | +++ | ++ |
| Example 3 | ++ | ++ |
| Comparative Example 1 | + | + |
| Treatment control |  |  |
| Positive control | + | + |
| Negative control | − | − |

In Table 2, the sign "−" indicates that no analgesic effect was observed, the sign "±" indicates that an analgesic effect comparable to the treatment control was observed, the sign "+" indicates that an analgesic effect comparable to the positive control was observed, the sign "++" indicates that a higher analgesic effect than the positive control was observed, and the sign "+++" indicates that a higher analgesic effect than "++" was observed.

Examples 1 to 3 maintained a higher analgesic effect at 30 and 90 minutes after administration than the treatment control. Comparative Example 1, which was prepared using the sucrose fatty acid ester in place of the sophorolipid, exhibited a lower analgesic effect than the compositions prepared using the sophorolipid. The results indicate that emulsification process using a sophorolipid is essential for the enhancement of the analgesic effect.

(3) Preparation of Compositions

The components and the emulsification temperature that are required for the enhancement of the analgesic effect were studied.

Example 4

The composition of Example 4 was prepared in the same manner as in Example 1 except that squalene was used as an oil phase and a mixture of the sophorolipid, bovine lactoferrin, sodium hydrogen carbonate and water was used as an aqueous phase in accordance with the components of Example 4 in Table 3 (see Table 3). The phases were then heated to 80° C. The aqueous phase was added to the oil phase that was stirred at a high speed with a high-speed stirrer to give the composition of Example 4.

Example 5

The composition of Example 5 was prepared in the same manner as in Example 4 except that soybean oil was used in place of squalene as the oil or fat of the oil phase.

Example 6

The composition of Example 6 was prepared in the same manner as in Example 4 except that the emulsification temperature was set at 60° C.

Example 7

The composition of Example 7 was prepared in the same manner as in Example 5 except that the emulsification temperature was set at 60° C.

Example 8

The composition of Example 8 was prepared in the same manner as in Example 6 except that the components of the oil phase and the aqueous phase were as described in Example 8 in Table 3.

Example 9

The composition of Example 9 was prepared in the same manner as in Example 7 except that the components of the oil phase and the aqueous phase were as described in Example 9 in Table 3.

TABLE 3

|  |  | Example 4 | Example 5 | Example 6 | Example 7 | Example 8 | Example 9 |
|---|---|---|---|---|---|---|---|
| Oil phase | Squalene | 2.50% | — | 2.50% | — | 2.50% | — |
|  | Soybean oil | — | 2.50% | — | 2.50% | — | 2.50% |
| Aqueous phase | Sophorolipid | 2.50% | 2.50% | 2.50% | 2.50% | 0.50% | 0.50% |
|  | Bovine lactoferrin | 5.00% | 5.00% | 5.00% | 5.00% | 5.00% | 5.00% |
|  | Sodium hydrogen carbonate | 0.20% | 0.20% | 0.20% | 0.20% | 0.10% | 0.10% |
|  | Water | q.s. for 100% | q.s. for 100% | q.s. for 100% | q.s. for 100% | q.s. for 100% | q.s. for 100% |
|  | Total | 100% | 100% | 100% | 100% | 100% | 100% |
|  | Emulsification temperature | 80° C. | 80° C. | 60° C. | 60° C. | 60° C. | 60° C. |

(4) Experiment 2: Evaluation of Analgesic Effect by Setting Different Emulsification Temperatures The tail-flick test was performed using the compositions of Examples 4 to 9 in the same manner as in Experiment 1, and the results are shown in Table 4.

TABLE 4

|  | Evaluation at 30 min | Evaluation at 90 min |
|---|---|---|
| Example 4 | ++ | ++ |
| Example 5 | ++ | +++ |
| Example 6 | +++ | +++ |
| Example 7 | +++ | +++ |
| Example 8 | ++ | ++ |
| Example 9 | + | ++ |

The analgesic effect was observed in the absence of lecithin or glycerol (Examples 4 to 9). The analgesic effect was also observed when squalene was replaced with soybean oil. The results indicate that the effect was exhibited using an oil other than squalene.

(5) Preparation of Compositions

Example 10

The composition of Example 10 was prepared in the same manner as in Example 1 except that the components of the oil phase and the aqueous phase were as described in Example 10 in Table 5. The cottonseed oil used was a cottonseed salad oil manufactured by Summit Oil Mill Co., Ltd.

Example 11

The composition of Example 11 was prepared in the same manner as in Example 1 except that the components of the oil phase and the aqueous phase were as described in Example 11 in Table 5. The cacao butter used was TC cocoa butter manufactured by Daito Cacao Co., Ltd.

Example 12

The composition of Example 12 was prepared in the same manner as in Example 1 except that the components of the oil phase and the aqueous phase were as described in Example 12 in Table 5. The medium-chain fatty acid glyceride used was PANACET 810 manufactured by NOF Corporation.

TABLE 5

|  |  | Example 10 | Example 11 | Example 12 |
|---|---|---|---|---|
| Oil phase | Cottonseed oil | 2.00% | — | — |
|  | Cacao butter | — | 2.00% | — |
|  | Medium-chain fatty acid glyceride | — | — | 2.00% |
|  | Soybean lecithin (50%) | 0.50% | 0.50% | 0.50% |
|  | Glycerol | 5.00% | 5.00% | 5.00% |
| Aqueous phase | Sophorolipid | 2.50% | 2.50% | 2.50% |
|  | Bovine lactoferrin | 5.00% | 5.00% | 5.00% |
|  | Sodium hydrogen carbonate | 0.20% | 0.20% | 0.20% |
|  | Water | q.s. for 100% | q.s. for 100% | q.s. for 100% |
|  | Total | 100% | 100% | 100% |

(6) Experiment 3: Evaluation of Analgesic Effect with Use of Oil or Fat Other than Squalene or Soybean Oil The tail-flick test was performed using the compositions of Examples 10 to 12 in the same manner as in Experiment 1, and the results are shown in Table 6.

The experimental results of Examples 10 to 12 are shown in Table 6.

TABLE 6

|  | Evaluation at 30 min | Evaluation at 90 min |
|---|---|---|
| Example 10 | ++ | ++ |
| Example 11 | ++ | ++ |
| Example 12 | ++ | ++ |

The analgesic effect was observed using the cottonseed salad oil, the cacao butter, or the medium-chain fatty acid in place of squalene. In the preparation of an emulsified product of the present invention, various types of oils can be used.

Examples of the application of the emulsified product of the present invention to foods will be described below.

1. Pudding

TABLE 7

| Formula | A |
|---|---|
| Gelatin | 3 g |
| Water | 15 g |
| Whole egg | 55 g |
| Milk | 144 g |
| Sugar | 30 g |
| Vanilla flavor | 0.5 g |
| Sophorolipid-emulsified product | 6 g |

Gelatin was soaked in water to bloom. Milk was heated, and the bloomed gelatin was added to the milk and dissolved therein. In a container, egg and sugar were placed and well beaten, and then the composition of Example 1 (sophorolipid-emulsified product) was mixed. To the mixture, the heated milk was added, and a flavor was added. The resulting mixture was poured into two cups and was cooled in a refrigerator to harden. The obtained pudding was 120 g per cup.

2. Chocolate

TABLE 8

| Formula | A | B |
|---|---|---|
| Commercial available bitter chocolate (shell) | 45 g | 45 g |
| Commercial available bitter chocolate (filling) | 43 g | 32.5 g |
| Almond |  | 4 g |
| Corn flakes |  | 5 g |
| Wheat puffs |  | 1.5 g |
| Sophorolipid-emulsified product powder | 12 g | 12 g |
| Total | 100 g | 100 g |

Equivalent amounts of the composition of Example 1 (sophorolipid-emulsified product) and β-cyclodextrin were mixed, and the mixture was processed into a powder with a spray dryer to give a sophorolipid-emulsified product powder. Bitter chocolate was melted over a hot water bath at 50 to 60° C. The cavities of a chocolate mold were filled with the chocolate, and the mold was flipped over to remove the excess chocolate. The mold was placed in a refrigerator to let the chocolate harden, thereby giving chocolate shells. The chocolate shells were filled with 4.5 g of a mixture of melted chocolate and the sophorolipid-emulsified product powder. The filled shells were covered with melted chocolate and the mold was cooled in a refrigerator to let the chocolate harden (formula A). The weight of one chocolate bonbon was about 10 g. To prevent deterioration of the texture due to addition of the sophorolipid-emulsified product powder, further ingredients such as wheat puffs, chopped nuts, corn flakes, etc. may be added together with the sophorolipid-emulsified product powder (formula B).

(7) Experiment 4: Evaluation of Effect of the Compositions of Present Invention for Promoting Intestinal Absorption of Physiologically Active Substances The effect of the compositions of the present invention of Examples 13 to 16 and Comparative Examples 2 to 9 for promoting intestinal absorption of physiologically active substances were evaluated using silica beads coated with a phosphatidylcholine.

Intestinal membrane transport plays a pivotal role in intestinal absorption. Intestinal membrane transport includes transport by passive diffusion through the cell membrane and the intercellular space as well as active transport by transporters. An essential factor for the cell membrane transport is the affinity of a substance with a biological membrane, which is mainly composed of phospholipids. The cell membrane transport has been assessed by measuring the octanol partition coefficient or the liposomal partition coefficient. The evaluation of the cell membrane transport has been recently carried out by measuring the difference in the retention of a substance on a column using a phospholipid as a ligand of the stationary phase. The liposomal partition coefficient has been described to highly correlate with the cell membrane transport.

In the evaluation herein, the binding of substances to silica beads coated with a phospholipid (phosphatidylcholine) was compared. A higher binding indicates a higher cell membrane transport and a higher intestinal absorption.

A. Methods

An aqueous phase was prepared and the pH was adjusted with a pH adjuster to a pH value of 6. The aqueous phase and an oil phase were heated to 50 to 60° C. The aqueous phase was added to the oil phase. The mixture was stirred with a homogenizer (HG-200, As One Corporation) at a high speed of 10,000 rpm for 10 minutes to give an emulsion.

The components of the compositions of Example and Comparative Examples including a water-soluble fluorescent substance (fluorescein Na) are shown in Table 9.

TABLE 9

|  |  | Example 13 | Comparative Example 2 | Comparative Example 3 |
|---|---|---|---|---|
| Oil phase | Squalene | 2.0% | 2.0% | — |
|  | Soybean lecithin | 0.5% | 0.5% | — |
|  | Sucrose fatty acid ester | — | 2.5% | — |
|  | Glycerol | 5.00% | 5.0% | — |
| Aqueous phase | Sophorolipid | 2.5% | — | — |
|  | Fluorescein Na salt | 0.0025% | 0.0025% | 0.0025% |
|  | pH adjuster | q.s. | — | — |
|  | Water | q.s. for 100% | q.s. for 100% | q.s. for 100% |
|  | Total | 100% | 100% | 100% |

A fluorescein Na salt is a water-soluble fluorescent substance, and was used as a model compound of a water-soluble physiologically active substance. The experimental results indicate that the present invention enables efficient absorption of a water-soluble physiologically active substance through the intestinal tract.

The affinity with phosphatidylcholine-coated silica beads (TRANSIL Intestinal Absorption Kit, SOVICELL GMBH) was assessed. A volume of 200 μl of PBS (phosphate buffered saline) containing the beads was added to each tube, and 20 μl of each of the compositions was added. The mixture was agitated with a test tube mixer for 12 minutes. The beads were allowed to settle, and the supernatant was collected and diluted to 10-fold. The fluorescence intensity of the supernatant was measured with a spectrophotometer (Hitachi F-2700, excitation wavelength: 494 nm, fluorescence wavelength: 521 nm). From the measurement results, the relative amount of the fluorescent substance of Example 13 or Comparative Example 2 bound to the beads was calculated, with the obtained value of an aqueous fluorescein Na solution (Comparative Example 3) taken as 1.

The components of the compositions of Example and Comparative Examples including a fat-soluble pigment (oil red) are shown in Table 10.

TABLE 10

|  |  | Example 14 | Comparative Example 4 | Comparative Example 5 |
|---|---|---|---|---|
| Oil phase | Squalene | 2.0% | 2.0% | 2.0% |
|  | Soybean lecithin | 0.5% | 0.5% |  |
|  | Sucrose fatty acid ester | — | 2.5% |  |
|  | Glycerol | 5.0% | 5.0% |  |
|  | Oil red | 0.01% | 0.01% | 0.01% |
| Aqueous phase | Sophorolipid | 2.5% | — |  |
|  | pH adjuster | q.s. | q.s. |  |
|  | Water | q.s. for 100% | q.s. for 100% |  |
|  | Methanol |  |  | q.s. for 100% |
|  | Total | 100% | 100% | 100% |

Oil red is a fat-soluble fluorescent substance, and was used as a model compound of a fat-soluble physiologically active substance. The experimental results indicate that the present invention enables efficient absorption of a fat-soluble physiologically active substance through the intestinal tract.

A volume of 200 μl of PBS containing the beads was added to each tube, and 20 μl of each of the compositions was added. The mixture was agitated with a test tube mixer for 12 minutes. The beads were allowed to settle, and the supernatant was removed. The beads were washed with PBS, and 200 μl of methanol was added to elute oil red from the beads. The absorbance of the oil red solution in methanol was measured at 510 nm with an ultraviolet spectrophotometer (Shimadzu UV-1200). The relative amount of the pigment of Example 14 or Comparative Example 4 bound to the beads was calculated, with the obtained value of an oil red solution (Comparative Example 5) taken as 1.

The components of the compositions of Example and Comparative Examples including tocopherol are shown in Table 11.

TABLE 11

|  |  | Example 15 | Comparative Example 6 | Comparative Example 7 |
|---|---|---|---|---|
| Oil phase | Squalene | 2.0% | 2.0% | 2.0% |
|  | Soybean lecithin | 0.5% | 0.5% |  |
|  | Sucrose fatty acid ester | — | 2.5% |  |
|  | Glycerol | 5.0% | 5.0% |  |
|  | Tocopherol | 1.0% | 1.0% | 1.0% |
| Aqueous phase | Sophorolipid | 2.5% | — |  |
|  | pH adjuster | q.s. | q.s. |  |
|  | Water | q.s. for 100% | q.s. for 100% |  |
|  | Methanol |  |  | q.s. for 100% |
|  | Total | 100% | 100% | 100% |

A volume of 200 µl of PBS containing the beads was added to each tube, and 20 µl of each of the compositions was added. The mixture was agitated with a test tube mixer for 12 minutes. The beads were allowed to settle, and the supernatant was removed. The beads were washed with PBS, and 200 µl of methanol was added to elute tocopherol from the beads. The amount of tocopherol was measured by HPLC (Shimadzu LC-10A series). The relative amount of tocopherol of Example 15 or Comparative Example 6 bound to the beads was calculated, with the obtained value of a tocopherol solution (Comparative Example 7) taken as 1.

The components of the compositions of Example and Comparative Examples including docosahexaenoic acid (DHA) are shown in Table 12.

TABLE 12

|  |  | Example 16 | Comparative Example 8 | Comparative Example 9 |
|---|---|---|---|---|
| Oil phase | DHA-70 | 2.0% | 2.0% | 2.0% |
|  | Soybean lecithin | 0.5% | 0.5% |  |
|  | Sucrose fatty acid ester | — | 2.5% |  |
|  | Glycerol | 5.0% | 5.0% |  |
|  | Tocopherol | 0.3% | 0.3% |  |
| Aqueous phase | Sophorolipid | 2.5% | — |  |
|  | pH adjuster | q.s. | q.s. |  |
|  | Water | q.s. for 100% | q.s. for 100% |  |
|  | Methanol |  |  | q.s. for 100% |
|  | Total | 100.0% | 100.0% | 100% |

A volume of 200 µl of PBS containing the beads was added to each tube, and 20 µl of each of the compositions was added. The mixture was agitated with a test tube mixer for 12 minutes. The beads were allowed to settle, and the supernatant was removed. The beads were washed with PBS, and 200 µl of hexane was added to elute DHA from the beads. The amount of DHA was measured by gas chromatography (Shimadzu GC-2014 series).

The relative amount of DHA of Example 16 or Comparative Example 8 bound to the beads was calculated, with the obtained value of a DHA solution (Comparative Example 9) taken as 1.

Tests were performed in the same manner as above by preparing an emulsion using the sophorolipid and a sucrose fatty acid ester together with each of the following: retinol, eicosapentaenoic acid, linoleic acid, coenzyme $Q_{10}$, β-carotene, astaxanthin, lycopene, theaflavin, isoflavone, anthocyanidin, catechin, proanthocyanidin, soybean saponin, a yucca extract, a *Sapindus mukorossi* extract, riboflavin, thiamine, ascorbic acid, glycosides from *Siraitia grosvenorii*, alanine, proline, glutamic acid, marine peptides, soybean peptides, whey peptides, zinc gluconate, copper gluconate, and iron citrate.

HPLC was used for the analysis of retinol, coenzyme $Q_{10}$, β-carotene, astaxanthin, lycopene, theaflavin, isoflavone, catechin, and saponin. A spectrophotometer was used for the analysis of anthocyanidin and proanthocyanidin. GC was used for the analysis of eicosapentaenoic acid and linoleic acid. A fluorescence spectrophotometer was used for the analysis of thiamine and riboflavin. LC-MS was used for the analysis of glycosides from *Siraitia grosvenorii*, amino acids, and peptides. An atomic absorption spectrophotometer was used for the analysis of zinc gluconate, copper gluconate, and iron citrate.

B. Results of Examples

The results of Examples are shown in Table 13. The relative amount of the physiologically active substance of each of Examples and Comparative Examples bound to the beads was calculated, compared with the case using the physiologically active substance alone. The calculated value was expressed by the symbols A, B and C. The affinities of the physiologically active substances were assessed by comparing the cases where each physiologically active substance was emulsified with a sucrose fatty acid ester or the sophorolipid and where each of the physiologically active substances was used alone. The results indicate that emulsification using a sophorolipid will result in higher affinities of the physiologically active substances with the beads and a higher absorption through the intestinal tract.

TABLE 13

| Evaluated physiological active substance | | Example (sophorolipid) | Comparative Example (sucrose fatty acid ester) |
|---|---|---|---|
| Substance | Category | | |
| Fluorescein Na | Water-soluble fluorescent substance | A | C |
| Oil red | Fat-soluble pigment | B | C |
| Tocopherol | Vitamin | A | C |
| Retinol | Vitamin | B | C |
| Docosahexaenoic acid | Polyunsaturated fatty acid | A | C |
| Eicosapentaenoic acid | Polyunsaturated fatty acid | A | C |
| Linoleic acid | Polyunsaturated fatty acid | A | C |
| Coenzyme $Q_{10}$ | Ubiquinone | A | C |
| β-carotene | Carotenoid | A | C |
| Astaxanthin | Carotenoid | B | C |
| Lycopene | Carotenoid | A | C |
| Theaflavin | Flavonoid | B | C |
| Isoflavone | Flavonoid | A | C |
| Anthocyanidin | Flavonoid | A | C |
| Catechin | Tannin | B | C |
| Proanthocyanidin | Tannin | B | C |
| Soybean saponin | Saponin | A | C |
| Yucca extract | Saponin | B | C |
| *Sapindus mukorossi* extract | Saponin | B | C |
| Riboflavin | Vitamin | B | C |
| Thiamine | Vitamin | B | C |
| Ascorbic acid | Vitamin | A | C |
| Glycosides from *Siraitia grosvenorii* | Terpenoid | B | C |
| Alanine | Amino acid | B | C |

TABLE 13-continued

| Evaluated physiological active substance | | Example (sophoro-lipid) | Comparative Example (sucrose fatty acid ester) |
|---|---|---|---|
| Substance | Category | | |
| Proline | Amino acid | B | C |
| Glutamic acid | Amino acid | A | C |
| Marine peptides | Peptide | B | C |
| Soybean peptides | Peptide | B | C |
| Whey peptides | Peptide | A | C |
| Zinc gluconate | Mineral | B | C |
| Copper gluconate | Mineral | B | C |
| Iron citrate | Mineral | B | C |

(A: affinity of 5.0-fold or more, B: affinity of not less than 2.0-fold and less than 5.0-fold, C: affinity of less than 2.0-fold)

The invention claimed is:

1. A composition comprising a sophorolipid, a physiologically active substance, and an oil or fat, wherein the sophorolipid is a mixture of an acidic sophorolipid and a lactonic sophorolipid, and wherein the proportion of acidic sophorolipid is 50 wt % or more relative to the total amount of the mixture of the sophorolipids.

2. The composition of claim 1, wherein the physiologically active substance exhibits an improved bioavailability.

3. The composition of claim 1, which is orally administered.

4. The composition of claim 1, wherein the physiologically active substance exhibits resistance to degradation by digestive juices.

5. The composition of claim 1, wherein the oil or fat is at least one or more oils or fats selected from the group consisting of squalene, soybean oil, rapeseed oil, cottonseed oil, sesame oil, safflower oil, sunflower oil, corn oil, rice bran oil, peanut oil, cacao butter, and medium-chain fatty acid glycerides having 8 to 10 carbon atoms.

6. The composition of claim 1, wherein the physiologically active substance is a physiologically active substance that is intestinally absorbable.

7. The composition of claim 6, wherein the physiologically active substance that is intestinally absorbable is lactoferrin.

8. The composition of claim 7, wherein the lactoferrin enhances the analgesic effect of morphine.

9. The composition of claim 1, wherein the physiologically active substance is
   a) a fat-soluble physiologically active substance selected from the group consisting of
   i) a vitamins selected from vitamin A, vitamin D, vitamin E, vitamin K, and derivatives thereof,
   ii) polyunsaturated fatty acids selected from the group consisting of docosahexaenoic acid, eicosapentaenoic acid, α-linolenic acid, γ-linolenic acid, linoleic acid, and arachidonic acid,
   iii) ubiquinones, menaquinones, and phylloquinones having an isoprenoid side chain,
   iv) carotenoids selected from the group consisting of α-carotene, β-carotene, γ-carotene, lycopene, β-cryptoxanthin, lutein, zeaxanthin, canthaxanthin, and astaxanthin,
   v) steroids selected from the group consisting of ergosterol and stigmasterol,
   vi) fat-soluble polyphenols selected from the group consisting of curcumin, quercetin, and cinnamic acid,
   vii) flavonoids selected from the group consisting of isoflavone, anthocyanidin, and hesperidin,
   viii) saponins obtained from plants selected from the group consisting of Panax notoginseng, Panax ginseng, soybeans, cucumbers, yucca, jiaogulan (Gynostemma pentaphyllum), and Sapindus mukorossi,
   ix) lignans selected from the group consisting of sesamin and sesaminol,
   triterpenes selected from the group consisting of cucurbitacin and limonene, and
   xi) α-lipoic acid, or
   b) a water-soluble physiologically active substance selected from the group consisting of
   i) a vitamins selected from the group consisting of vitamin $B_1$, vitamin $B_2$, niacin, pantothenic acid, vitamin $B_6$, biotin, folic acid, vitamin $B_{12}$, vitamin C, and derivatives thereof,
   ii) amino acids selected from the group consisting of glycine, alanine, valine, leucine, isoleucine, phenylalanine, tyrosine, tryptophan, serine, threonine, proline, hydroxyproline, cysteine, methionine, aspartic acid, glutamic acid, lysine, arginine, histidine, and carnitine,
   iii) polyphenols, flavonoids and flavonoid glycosides selected from the group consisting of chlorogenic acid, tannin, catechin, flavonoid, lignan, lignin, coumarin, and theaflavin,
   iv) peptides selected from the group consisting of a soybean peptide, a sardine peptide, a marine peptide, a casein phosphopeptide, a whey peptide, a wheat peptide, and a corn peptide,
   v) triterpene glycosides selected from the group consisting of those derived from Siraitia grosvenorii and licorice, and
   vi) minerals selected from the group consisting of calcium, magnesium, iron, zinc, potassium, sodium, copper, vanadium, manganese, selenium, molybdenum, cobalt, and compounds to which these minerals are bound.

10. The composition of claim 1, which is a medicament.

11. The composition of claim 1, which is a food product.

12. The composition of claim 1, which is a supplement.

13. A method for producing the composition of claim 1, the method comprising mixing a sophorolipid, a physiologically active substance, and an oil or fat wherein the sophorolipid is a mixture of an acidic sophorolipid and a lactonic sophorolipid, and wherein the proportion of acidic sophorolipid is 50 wt % or more relative to the total amount of the mixture of the sophorolipids.

14. The composition of claim 9, wherein the phylloquinone is coenzyme Q10.

15. The composition of claim 1, wherein the proportion of acidic sophorolipid is 70 wt % or more relative to the total amount of the mixture of the sophorolipids.

16. The composition of claim 1, wherein the proportion of acidic sophorolipid is 80 wt % or more relative to the total amount of the mixture of the sophorolipids.

17. The composition of claim 1, wherein the proportion of acidic sophorolipid is 90 wt % or more relative to the total amount of the mixture of the sophorolipids.

* * * * *

UNITED STATES PATENT AND TRADEMARK OFFICE
CERTIFICATE OF CORRECTION

PATENT NO. : 10,307,466 B2  
APPLICATION NO. : 15/124432  
DATED : June 4, 2019  
INVENTOR(S) : Yasushi Suzuki et al.

Page 1 of 1

It is certified that error appears in the above-identified patent and that said Letters Patent is hereby corrected as shown below:

In the Claims

Column 21, Line 49, "i) a vitamins" should be -- i) vitamins --.

Column 22, Line 11, "triterpenes" should be -- x) triterpenes --.

Signed and Sealed this  
Thirtieth Day of June, 2020

Andrei Iancu  
*Director of the United States Patent and Trademark Office*